United States Patent [19]

Jones

[11] 3,968,012

[45] July 6, 1976

[54] AEROSOL BACTERIAL CONTAMINATION TEST KIT

[76] Inventor: Jay A. Jones, 4141 W. Mercer Way, Mercer Island, Wash. 98040

[22] Filed: June 6, 1975

[21] Appl. No.: 584,372

[52] U.S. Cl. ............................... 195/142; 195/127
[51] Int. Cl.² .......................................... C12B 1/02
[58] Field of Search ........................... 195/127, 142

[56] References Cited
UNITED STATES PATENTS

| | | | |
|---|---|---|---|
| 2,865,816 | 12/1958 | Stefanye et al. | 195/142 |
| 3,127,329 | 3/1964 | Andersen | 195/142 |

*Primary Examiner*—Alvin E. Tanenholtz
*Attorney, Agent, or Firm*—Christensen, O'Connor, Garrison & Havelka

[57] ABSTRACT

An inexpensive disposable test kit for conveniently collecting airborne aerosol particulates on a bacteriological culture medium for determining the bacterial contamination of effluent air from respiratory equipment in hospitals and clinics. A collecting dish erves as a removable bottom on a cylindrical casing or main body. The latter has an integral guide funnel supported in its open upper end for directing the affluent stream downwardly against the culture medium in the dish. Apertures in an annular supporting web for the guide funnel, together with the convergence of the funnel with the casing wall help induce the flow of effluent in a pattern giving predictable or measured exposure of the culture medium to contact by the aerosol particulates. A removable sanitary cap for the funnel end of the casing serves subsequently as a protective cover for the culture medium dish when the latter is detached as a petri dish carrying the culture thus collected for incubation and examination.

10 Claims, 4 Drawing Figures

AEROSOL BACTERIAL CONTAMINATION TEST KIT

BACKGROUND OF THE INVENTION

The present invention relates to a disposable aerosol bacterial contamination test apparatus for the reliable or measured collecting of air stream sample particulates on a bacteriological culture medium for the purpose of determining bacterial contamination of the air stream and/or its source equipment. The invention is herein illustratively described by reference to the presently preferred embodiment thereof; however it will be recognized that certain changes may be made therein with respect to details without departing from the essential features involved.

Residual contamination in hospital respiratory machines such as ventilators and anesthesia gas machines can communicate lung infections. Such machines normally employ water reservoirs and humidifying devices which function to deliver to the patient breathing gases containing moisture in the form of aerosol particles. The moist, warm environment provided in the breathing circuits of such machines provides ideal environment for the growth of various pathogenic organisms that can cause lung infections. Typical of these nosocomial respiratory infections is bacterial pneumonia.

Obviously, in addition to frequent antiseptic decontamination of medical ventilating equipment, a vigorous bacteriological surveillance program is essential, a program in which the equipment undergoes regular testing for the growth of pathogenic organisms. The sterilization, assembly and preparation of conventional reusable culturing equipment is, however, time-consuming and inconvenient for laboratory technicians. As a result, hospital programs for bacterial surveillance of ventilating equipment, commonly acknowledged as being essential for patient protection, are sometimes conducted less vigorously than prudence dictates.

A common method of testing equipment for bacterial growth is to take swab cultures. In this method, sampling is conducted by rubbing cotton swab sticks on various surfaces of the ventilating equipment, reservoirs, tubing, face masks and other components. The swabs are then smeared on the surface of a culture medium in a petri dish which is subsequently incubated for a period of time and then checked for bacterial growth. The swab method, however, only tests for surface contamination and may not reveal whether there is contamination in the aerosol gases that are delivered to the patient by the machine. As a result, the so-called aerosol sampling method is preferred over the swab technique. The aerosol method permits direct sampling of the aerosol effluent carried from the machine to the patient's respiratory tract, and thus provides a more reliable test.

Aerosol sampling is commonly conducted by sampling and incubation on a culture medium, such as agar, poured into a test tube where it is allowed to harden. In one technique a funnel is then placed loosely in the top of the test tube and the flexible feed tube from the ventilating machine placed against the funnel feeds effluent gas into the test tube. The effluent impinges on the culture medium which collects the particulates, and, then exhausts from the open end of the test tube around the funnel. While an attempt is made to regularize or standardize the rate at which particles are collected on the medium the pattern of flow in the test tube exposing the medium to the particles is variable because of varying placement of the funnel in the mouth of the test tube. This introduces a variable in the collection process that lends a degree of uncertainty in the quantitative aspects of the test. Moreover, as stated above, the inconveniences of preparing, assembling and using the disassociated components is also a deterrent to consistently diligent testing.

It is an object of the present invention, therefore, to provide a reliable, easy-to-use, inexpensive and disposable test kit which incorporates all of the functional features required for the performance of aerosol bacteriological sampling and subsequent incubation and examination processes.

A further object is to provide an aerosol test container device so formed as to induce a regularized and efficient columnar flow effluent gases against the collecting culture medium in the bottom thereof, by channeling the outflow of such gases away from the incident flow.

It is an additional object to provide a kit assembly in which the components are available and organized to facilitate performing each of the successive process steps in making a complete test.

SUMMARY OF THE INVENTION

In accordance with the foregoing objects and other objects that will become apparent, the invention provides a disposable aerosol bacterial contamination test apparatus in kit form comprising a culture medium dish bottom member having a sliding press fit with the bottom of a cylindrical main body member incorporating an integral funnel in its top for channeling input flow, having apertures in the supporting web of the funnel for exhausting aerosol effluent gases having impinged on the culture medium, and a removable sanitary cover member that can serve also as a protection cover for the culture medium dish member for use of the latter as a petri dish bacterial incubator.

DESCRIPTION OF THE DRAWINGS

The presently preferred embodiment of the invention is illustrated in the attached drawings, wherein.

DESCRIPTION OF THE PREFERRED EMBODIMENT

Figure 1:
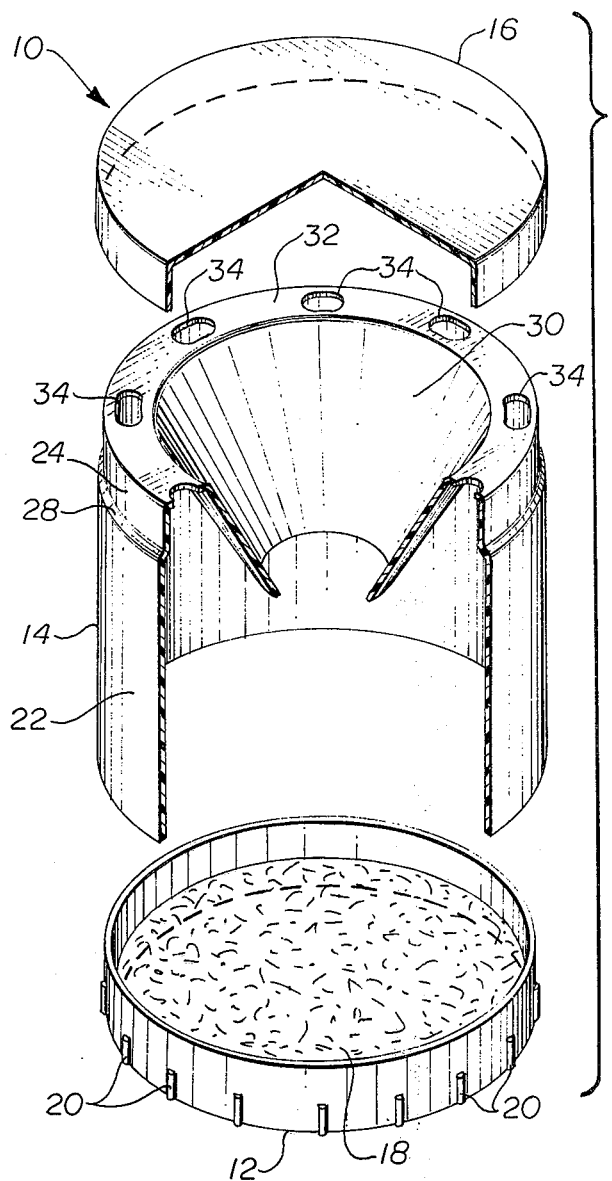
FIG. 1 is an isometric view of the aerosol bacterial contamination kit device of the present invention with the parts separated.

Referring first to FIG. 1, the aerosol bacterial contamination test apparatus 10 of the present invention is comprised of three components; a culture medium dish 12, a cylindrical casing 14, and a sanitary cover 16, each molded of, for example, polystyrene plastic. The culture medium dish 12 has a flat bottom and a low surrounding side wall of cylindrical form open at the top. The dish, resembling the dish portion of a common laboratory petri dish used for plate cultures, contains a culture medium 18 of, for example, tripticase soy agar. The outside diameter of the rim of dish 12 approximates the inside diameter of the lower end of casing 14, such that the dish will have a sliding press fit in the open lower end of the cylindrical casing 14 to form an essentially airtight joint. Splines 20, formed on the outer surface of the dish, limit the extent to which the dish may be inserted up into the cylindrical casing 14.

The right cylinder tubular casing 14, as with the culture medium dish, is molded of a single piece of plastic. It is comprised of circular cylindrical tubular section 22 having a step reduction of diameter over a short section 24 near the top. The wall of sanitary cover 16 slidably but tightly fits around the section 24, seating on the shoulder 28 formed at the step or junction between the two sections of the casing.

A re-entrant funnel member 30 is formed centrally within the open upper end of casing 14, supported in that position by an annular web 32 extending transversely between the upper peripheries, the casing 14 and upper edge of funnel member 30. Apertures 34, formed in the web 32 provide for exhaust of effluent flowing first downwardly through the funnel exit into impact with the culture medium 18 in the dish member 12. These apertures thereby provide a directing influence on the flow, inducing a pattern of motion in which the gases impinging the agar are withdrawn radially outward, thence upwardly along the inside wall of casing 14. Convergence of the space between the funnel and the casing wall enhances the outflow of gases through apertures 34 and assists in maintaining columnar downward flow of the input stream against the collecting medium 18. The detachable sanitary cover 16 is preferably molded of transparent plastic material. Though tightly fitted to the top of casing 14, cover 16 preferably fits somewhat loosely on the petri dish bottom cup 12 when the latter is withdrawn with a specimen to be incubated.

Figure 2:
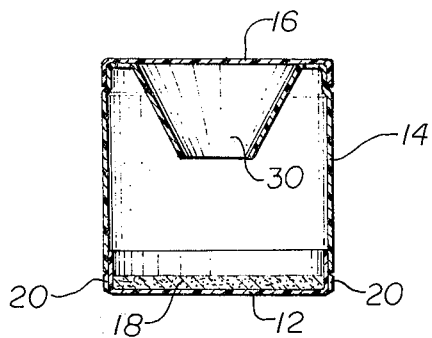
FIG. 2 is a cross-sectional side elevation view of the apparatus of FIG. 1 illustrating the elements as they would be configured in a packaged state prior to use.

The aerosol bacterial contamination test apparatus of this invention is initially packaged for storage in the assembled condition of the parts as depicted in FIG. 2 and sealed in a sterile plastic bag (not shown). As thus presented to the user, the culture medium bottom dish 12, about nominally 15 mm deep, has a predeposited layer of medium 18 about 4 mm deep.

Figure 3:
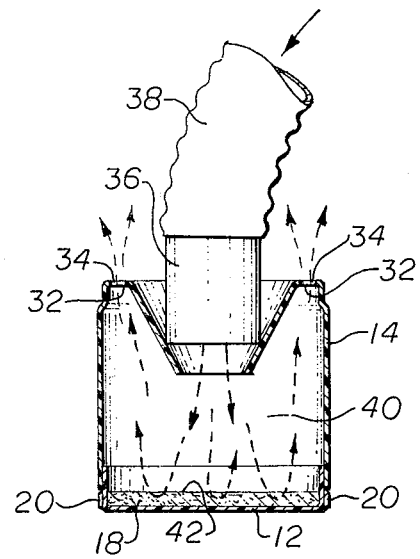
FIG. 3 is a view similar to FIG. 2 illustrating the elements of the apparatus as they would be configured to interface with a ventilating machine effluent discharge tube for sampling of the aerosol effluent issuing therefrom.

For use, the apparatus is removed from its sterile package and the sterile cover 16 is removed to provide access to the funnel portion 30 of the main body cylinder 14 as shown in FIG. 3. The end fitting 36 of the discharge hose 38 of a ventilating machine to be tested is then pressed down into the entrance funnel 30 so as to direct gases and particulates carried thereby through the funnel, downwardly along the axis of casing 14 at the center of plenum space 40 and against the culture medium 18. The induction effect of apertures 34 discharging the gases from around the funnel, and the funnel's own upward convergance with the wall of casing 14 tend to columnate the downward flow against the agar so as to establish a definite and fairly predictable exposure rate of the agar to suspended particulates carried by the gas. Thus, test sample accumulation time can be predictably related to the equipment being tested and the conditions of the sampling.

Figure 4:
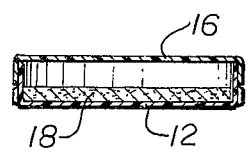
FIG. 4 is a cross-sectional side elevation view of the covered culture medium dish serving as a petri dish for incubation and examination purposes.

When the sampling is complete, the ventilating machine feed tube 38 is removed from its contact with the main body cylinder funnel 30 and the culture medium dish portion 12 of the apparatus is disengaged from the main body cylinder 14, which is subsequently discarded. The clear plastic sanitary cover 16 previously installed on the now discarded main body cylinder, is then loosely installed on the culture medium dish member as shown in FIG. 4. The petri dish thus formed by the covered dish containing the contaminated medium is subsequently incubated, examined and may then be discarded.

The apparatus of the present invention may be produced in a variety of physical configurations of varying sizes and configurations according to choice and to suit different needs. Hence while the present invention has been described in relation to its preferred embodiment, it is intended that the novel concepts thereof be interpreted with equivalent variations in view consistent with the definitions of the appended claims.

What is claimed is:

1. A disposable kit for sterile sampling and culturing of gas-borne microorganisms and the like, comprising a rimmed, flat and shallow tray having an internal bottom coating thereon of microorganism culture medium, a removable cover for said tray, and an enclosed gas-flow directing chamber having one end open to which the tray is removably fitted so as to protectively close said one end in substantially airtight relationship, having an opposite end open to which the tray cover is removably fitted so as to protectively close said opposite end in substantially airtight relationship in pre-use storage thereof, said opposite end having inlet orifice means rimmed by an inwardly convergent exteriorly presented chamber wall defining a locating funnelling receptacle for placement of the end of a gas supply hose so as to direct gases from the hose through said inlet orifice into the chamber interior, and said opposite end further having an outlet orifice means formed therein adjacent to but separated by said wall from said inlet orifice, for the discharge of gases from the chamber after such gases have flowed against said tray interior.

2. The kit defined in claim 1 wherein the inlet orifice means has a central axis substantially perpendicular to the plane of the orifice, the tray on said one end of the chamber being disposed substantially perpendicular to said axis.

3. A device for test sampling of gas-borne bacterial particulates and the like comprising a generally cylindrical casing adapted for positioning with its axis upright, a bottom closure member on the lower end of the casing having a bacterial culture medium deposited thereon, a downwardly convergent funnel member positioned centrally within the upper end of said casing to form an upwardly convergent annular space therebetween and having a central opening to admit a gas stream from an external source directed downwardly into the casing, and support means on the casing projecting inwardly to support the funnel member in such position and forming open spaces distributed around the funnel member for exiting of gas rising upwardly adjacent the interior of the casing into said convergent annular space.

4. The test device defined in claim 3, wherein the bottom member has a flat bottom and an upright cylindrical wall in sliding press fitted engagement with the casing to be removable therefrom.

5. The test device defined in claim 3, and a cover cap having a sliding press fitted engagement with the casing covering the funnel member and to be removable from the casing.

6. The test device defined in claim 3, wherein the cover cap fits over the bottom member as a cap with the bottom member removed from the casing.

7. The test device defined in claim 6, wherein the casing, funnel member and support means are of integral one-piece construction.

8. The test device defined in claim 7, wherein the support means comprises a multiply-apertured annular web bridging integrally between the upper ends of the casing and funnel member.

9. The test device defined in claim 3, wherein the support means comprises a multiply-apertured annular web bridging integrally between the upper ends of the casing and funnel member.

10. The device defined in claim 9, wherein the casing near its upper end has a step reduction in outer diameter, a cover cap with an annular wall initially slidably fitted tightly over the upper end of the casing, and wherein the bottom member has an annular wall that seats inside the lower end of the casing and has an outside diameter slightly smaller than the inside diameter of the cover cap annular wall.

* * * * *